(12) United States Patent
Marmé

(10) Patent No.: US 7,329,505 B2
(45) Date of Patent: Feb. 12, 2008

(54) SPECIFIC DETECTION OF PROTEOLYTIC ENZYMES

(75) Inventor: Nicole Marmé, Peterstaler Strasse 168, 69118 Heidelberg (DE)

(73) Assignees: Jürgen Wolfrum, Rosdorf-Obernjesa (DE); Jens-Peter Knemeyer, Heidelberg (DE); Markus Sauer, Heldelberg (DE); Nicole Marme, Heldelberg (DE)

( * ) Notice: Subject to any disclaimer, the term of this patent is extended or adjusted under 35 U.S.C. 154(b) by 249 days.

(21) Appl. No.: 10/474,263

(22) PCT Filed: Apr. 8, 2002

(86) PCT No.: PCT/EP02/03882

§ 371 (c)(1),
(2), (4) Date: Apr. 19, 2004

(87) PCT Pub. No.: WO02/081509

PCT Pub. Date: Oct. 17, 2002

(65) Prior Publication Data

US 2005/0176926 A1    Aug. 11, 2005

(30) Foreign Application Priority Data

Apr. 6, 2001    (DE)    ................ 101 17 430

(51) Int. Cl.
  C12Q 1/37    (2006.01)
  G01N 21/76    (2006.01)
  H04B 7/14    (2006.01)
  A61K 38/00    (2006.01)
  C07K 17/00    (2006.01)

(52) U.S. Cl. ................ 435/23; 436/172; 455/24; 530/345; 530/409

(58) Field of Classification Search ............ None
See application file for complete search history.

(56) References Cited

U.S. PATENT DOCUMENTS 4,557,862 A * 12/1985 Mangel et al. ............ 530/331
5,856,083 A * 1/1999 Chelsky et al. ............ 435/4

FOREIGN PATENT DOCUMENTS

EP    0 428 000 A    5/1991

OTHER PUBLICATIONS

Craig et al. General Protease Assay Method Coupling Solid-Phase Substrate Extraction and Capillary Electrophoresis; Analytical Chemistry, vol. 70 (1998) pp. 3824-3827.*
Henegariu et al. Custom Fluorescent-Nucleotide Synthesis as an Alternative Method for Nucleic Acid Labeling; Nature Biotechnology, vol. 18 (2000) pp. 345-348.*
Jan Karolin, Lennart B.-A. Johansson, Leif Strandberg and Tor Ny, J. Am. Chem. Soc., 1994, 116, pp. 7801-7806, "Fluorescence and Absorption Spectroscopic Properties of Dipyrrometheneboron Difluoride (BODIPY) Derivatives in Liquids, Lipid Membranes, and Proteins".
Steven P. Leytus, L. Lee Melhado and Walter F. Mangel, Biochem. J. 1983, 209, pp. 299-307, "Rhodamine-based compounds as flurogenic substrates for serine proteinases".
Steven P. Leytus, Willima L. Patterson and Walter F. Mangel, Biochem. J. 1983, 215, pp. 253-260, "New class of sensitive and selective fluorogenic substrates for serine proteinases".
R. Müller, C. Zander, M. Sauer, M. Deimel, D.-S. Ko, S. Siebert, J. Arden-Jacob, G. Deltau, N.J. Marx, K.H. Drexhage and J. Wolfrum, Chemical Physics. Letters 262, Nov. 29, 1996, pp. 716-722, "Time-resolved identification of single molecules in solution with a pulsed semiconductor diode laser".
George W. Anderson, Joan E. Zimmermann and Francis M. Callahan, Am. Chem. Soc., May 5, 1964, "The Use of Esters of N-Hydroxysuccinimide in Peptide Synthesis".
Michael Ng et al.: "A fluorescent Oligopeptide Energy Transfer Assay with Broad Applications for Neutral Proteases", in: Analytical Biochemistry, vol. 183, No. 1, 1989.

* cited by examiner

*Primary Examiner*—Jon Weber
*Assistant Examiner*—Paul Martin
(74) *Attorney, Agent, or Firm*—Henry M. Feiereisen; Ursula B. Day

(57) ABSTRACT

Specific detection of proteolytic enzymes is achieved by extinguishing dye fluorescence by the amino acid tryptophan. Ttuyptophan is disposed on one side of the cutting site of a proteolytic enzyme while an amino acid marked with a dye is arranged on the other side. Extinction of fluorescence occurs prior to enzyme cutting. Spatial separation of the tryptophan and the dye takes place after cutting, whereby fluorescence extinction does not occur. The dye can then fluoresce and a signal increase occurs thereby indicating that cutting has been carried out and the presence of the enzyme.

5 Claims, 4 Drawing Sheets

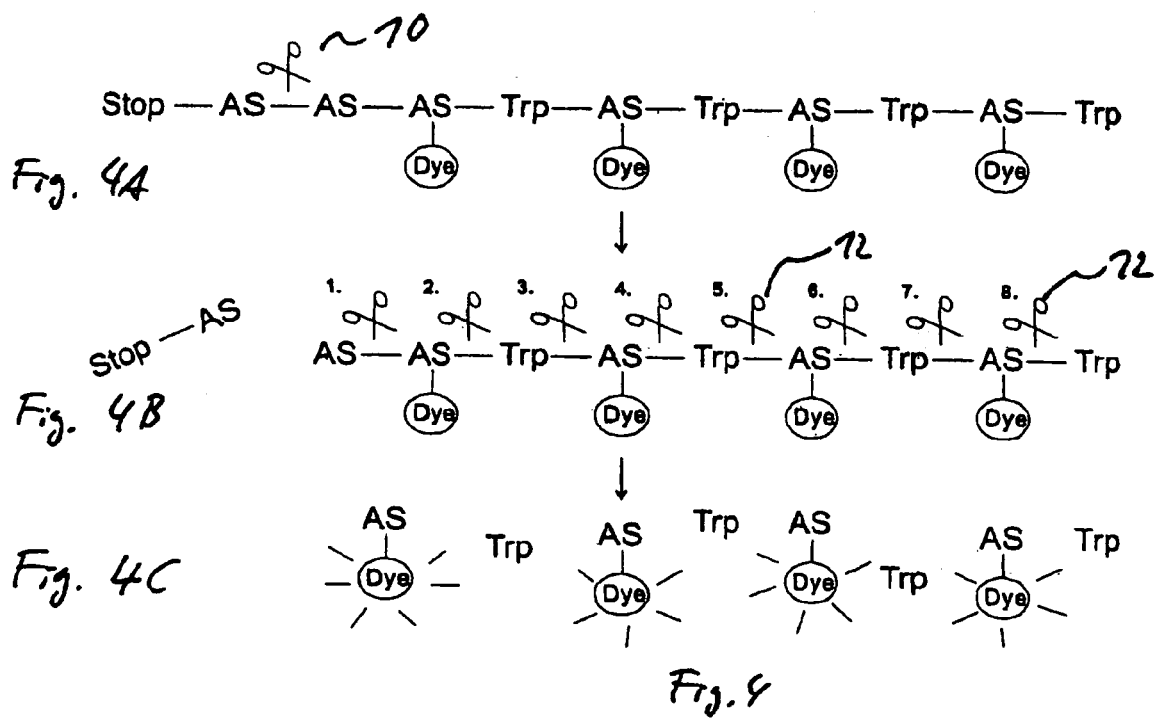

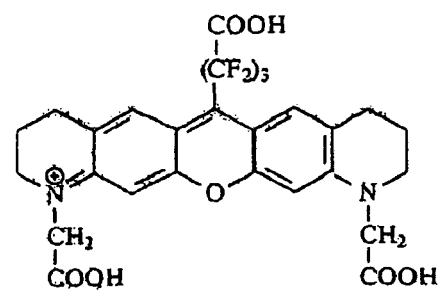
JA 165
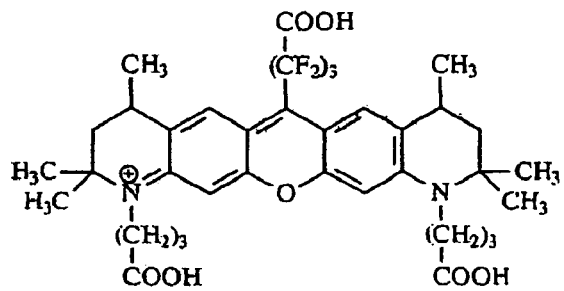
JA 167
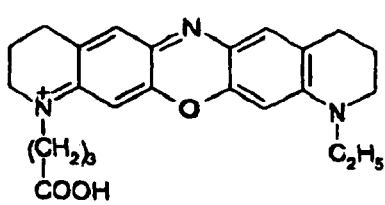
MR 121
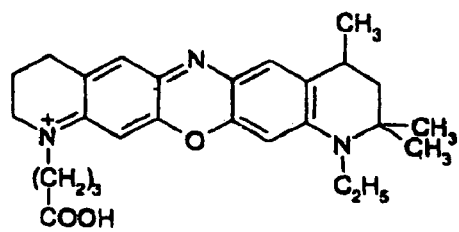
JA 242
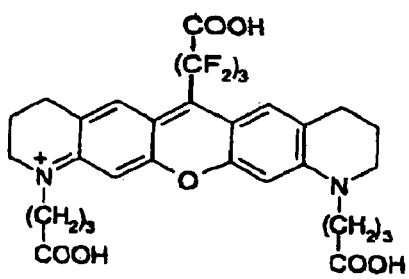
JA 169
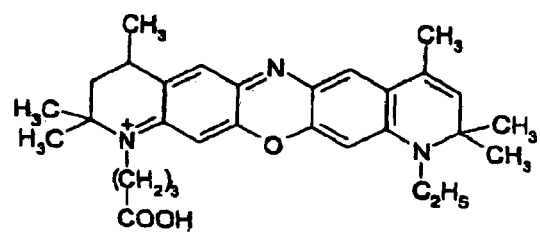
JA 243
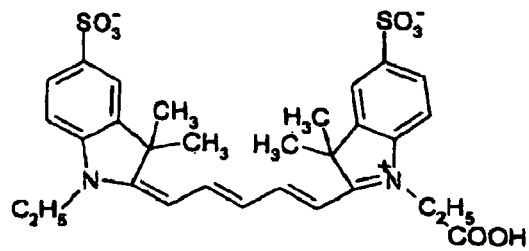
Cy5
Fig. 5

SEQUENCE LISTING

```
<160> NUMBER OF SEQ ID NOS: 7

<210> SEQ ID NO 1
<211> LENGTH: 12
<212> TYPE: PRT
<213> ORGANISM: Human immunodeficiency virus
<220> FEATURE:
<221> NAME/KEY: PEPTIDE
<222> LOCATION: (1)..(12)
<223> OTHER INFORMATION: EDANS dye donor is between positions 2 and 3.
      DABCYL dye acceptor is between positions 11 and 12

<400> SEQUENCE: 1

Arg Glu Ser Gln Asn Tyr Pro Ile Val Gln Lys Arg
1               5                   10

<210> SEQ ID NO 2
<211> LENGTH: 6
<212> TYPE: PRT
<213> ORGANISM: Human immunodeficiency virus
<220> FEATURE:
<221> NAME/KEY: PEPTIDE
<222> LOCATION: (1)..(6)
<223> OTHER INFORMATION: EDANS dye donor is located between amino acids
      2 and 3

<400> SEQUENCE: 2

Arg Glu Ser Gln Asn Tyr
1               5

<210> SEQ ID NO 3
<211> LENGTH: 6
<212> TYPE: PRT
<213> ORGANISM: Human immunodeficiency virus
<220> FEATURE:
<221> NAME/KEY: PEPTIDE
<222> LOCATION: (1)..(6)
<223> OTHER INFORMATION: DABCYL dye acceptor is located between amino
      acids 5 and 6.

<400> SEQUENCE: 3
```

```
Pro Ile Val Gln Lys Arg
1               5

<210> SEQ ID NO 4
<211> LENGTH: 5
<212> TYPE: PRT
<213> ORGANISM: Human immunodeficiency virus
<220> FEATURE:
<221> NAME/KEY: PEPTIDE
<222> LOCATION: (1)..(5)

<400> SEQUENCE: 4

Gln Lys Arg Arg Trp
1               5

<210> SEQ ID NO 5
<211> LENGTH: 12
<212> TYPE: PRT
<213> ORGANISM: Human immunodeficiency virus
<220> FEATURE:
<221> NAME/KEY: PEPTIDE
<222> LOCATION: (1)..(12)
<223> OTHER INFORMATION: MR 121 is located between amino acids 1 and 2

<400> SEQUENCE: 5

Lys Trp Ser Gln Asn Tyr Pro Ile Val Gln Pro Pro
1               5                   10

<210> SEQ ID NO 6
<211> LENGTH: 6
<212> TYPE: PRT
<213> ORGANISM: Human immunodeficiency virus
<220> FEATURE:
<221> NAME/KEY: PEPTIDE
<222> LOCATION: (1)..(6)
<223> OTHER INFORMATION: MR 121 is located between  amino acids 1 and 2

<400> SEQUENCE: 6

Lys Trp Ser Gln Asn Tyr
1               5

<210> SEQ ID NO 7
<211> LENGTH: 6
<212> TYPE: PRT
<213> ORGANISM: Human immunodeficiency virus
<220> FEATURE:
<221> NAME/KEY: PEPTIDE
<222> LOCATION: (1)..(6)

<400> SEQUENCE: 7

Pro Ile Val Gln Pro Pro
1               5
```

SPECIFIC DETECTION OF PROTEOLYTIC ENZYMES

BACKGROUND OF THE INVENTION

Proteolytic enzymes are proteases or peptidases, i.e. enzymes that are able to split or lyse peptides or proteins. The word "peptide" generally denotes a shorter amino acid sequence, whereas the word "protein" generally denotes larger molecules consisting of an amino acid sequence. Both terms are used synonymously in the following.

Peptidases and proteases play a decisive role in protein activation, cell regulation and signal transmission. Their detection at maximum possible sensitivity is therefore of enormous importance for understanding the functioning of a cell and its communication, and for monitoring the course of diseases.

Furthermore, precise knowledge of peptidase or protease concentration permits the targeted development of new therapeutic agents for inhibition, e.g. of HIV protease. HIV protease breaks down the HIV protein, which is at first very long after multiplication in a cell, into functioning individual proteins, which only then permit the further activity and growth of the HIV virus. There are two possible approaches. Firstly, if the HIV protease is blocked, the HIV virus cannot replicate and its propagation is halted. Secondly, infection with the HIV virus can take place via detection of the HIV protease. Specific detection of HIV protease can therefore serve as an AIDS test.

Moreover, protease tests are attracting increasing attention in medical research, because more and more diseases, including cancers, are being connected with enzymes. Tumor-associated proteases are increasingly the object of oncological-biochemical research. These proteases bring about the breakdown of proteins of the tumor stroma and of the basal membrane and thus permit tumor cell invasion. Therefore investigations of protease systems that are overexpressed in tumor cells are among the new prognosis factors in tumor diagnostics.

Another important aspect is the use of protease tests in quality control of biochemical products. If, for example proteins, enzymes, peptides, etc. are being sold, it is necessary to ensure that the products sold are free from proteases, so that the product sold does not break down on its own. The same can be used for testing the specific activity of proteases, e.g. after prolonged storage, regarding the question as to whether the enzymes are still active.

The proteolytic enzymes are divided into endopeptidases (proteases) and exopeptidases. Endopeptidases cleave amino linkages inside peptides. Exopeptidases digest peptides amino acid by amino acid starting from their ends, i.e. they cleave terminal amino acids. The exopeptidases can be further subdivided into aminopeptidases and carboxypeptidases, as claimed in their activity at the amino or N end or at the carboxy or C end of the peptide.

For determination of the concentration or activity of various peptidases and proteases, to date various fluorescence-based tests have been developed, and their operating principles and sensitivities are briefly described below.

One possibility for detecting proteolytic enzymes is offered by the "ENZCHEK® Protease Assay Kit" from the company Molecular Probes (Eugene, USA). For detecting proteases, this kit employs casein derivatives, to which very many pH-insensitive green or red fluorescing BODIPY® dyes are coupled (Karolin J., Johansson B. A., Strandberg L., Ny T.; J. Am. Chem. Soc., 1994, 116, 7801-7806). On account of the very high degree of marking of the protein, the intermolecular distances between the fluorophores are very small (typically of the order of a few nanometers). The dyes therefore extinguish each other, inter ella by dimer formation. Casein is a large enzyme, which contains many binding sites for proteases, because it has many different sequence segments. If the dye-marked casein derivative comes into contact with proteases, e.g. with trypsin, which hydrolyzes peptide bonds of the basic amino acids arginine and lysine on the carboxy side, these split the casein derivative into smaller peptides, so that as a rule the distance between the dyes increases. Extinction does not occur, and an increase in fluorescence is observed, indicating that proteolytic enzymes are present. For trypsin, for example, the detection sensitivity of this kit is a few ng/ml. For these small quantities of protease the detection time or measurement time is more than 10 hours. This test detects many proteolytic enzymes nonspecifically, since casein is digested by elastase, pepsin, thermolysin, papain, trypsin, etc.

An enzyme test based on Rhodamine 110 for various proteases and peptidases (Leytus S. P., Melhado L. L., Mangel W. F.: Rhodamine-based compounds as fluorogenic substrates for serine protease, (1983) Biochem. J., 209 (2): 299-307; Leytus S. P., Patterson W. L., Mangel W. F.: New class of sensitive and selective fluorogenic substrates for serine proteinases. Amino acid and dipeptide derivatives of rhodamine, (1983) Biochem. J., 215 (2): 253-260) is also being marketed for the detection of serine proteases. In this test, at least one of the amino groups of Rhodamine 110 is coupled covalently to an amino acid (usually arginine), causing strong extinction of the fluorescence of the fluorophore. After digestion of the peptide bonds there is a dramatic increase in fluorescence of Rhodamine 110. For caspase-3, the sensitivity of the test is a few ng absolute quantity of enzyme. Disadvantages are that the principle is not of general applicability, sometimes its action is nonspecific, and it is relatively insensitive.

A protease or peptidase test can also be accomplished by means of Forster fluorescence resonance energy transfer (FRET) (Forster Th.: Zwischenmolekulare Energiewanderung und Fluoreszenz [Intermolecular Energy Transfer and Fluorescence], (1948) Annalen der Physik, 2: 55-75). In this, the specific identification sequence of an endopeptidase is marked covalently at both ends with a donor dye and an acceptor dye. Owing to spectral overlap of donor emission with acceptor absorption, the fluorescence of the donor is extinguished at small distances. If the peptide is cleaved by the endopeptidase, the spatially close contact between donor and acceptor is lost, leading to an increase in fluorescence. Detection of HIV protease will be briefly explained here, as an example. The specific cleaving sequence of HIV protease is coupled, near the cleavage site, with an The peptide sequence is then: Arg-Glu(EDANS)-Ser-Gln-Asn-Tyr-Pro-Ile-Val-Gln-Lys-(DABCYL)-Arg SEQ ID NO: 1, using the 3-letter abbreviations for the amino acids. After cleavage by the HIV protease we have two parts: Arg-Glu(EDANS)Ser-Gln-Asn-Tyr-OH SEQ ID NO: 2 and Pro-Ile-Val-Gln-Lys(DABCYL)-Arg SEQ ID NO: 3. Suitable small distance between the two dyes. Sensitivity is of the order of nanomolar solutions of HIV protease. A disadvantage is the expensive synthesis of the substrate with specific coupling of a donor and an acceptor. If the substrate is to some extent marked incompletely, e.g. with just one donor, this leads to poor sensitivity of the test.

The aim of the invention is to improve the possibilities for a specific detection of proteolytic enzymes.

This aim is achieved by the inventions as claimed in the independent claims. Advantageous developments are described in the subclaims.

SUMMARY OF THE INVENTION

A first method of detection ("test" for short) is used for the detection of endopeptidases (also briefly referred to as enzymes hereinafter) by means of special peptides.

For this purpose, a peptide is prepared with the properties enumerated below. The peptide contains an identification sequence of the endopeptidase that is to be detected, and can therefore serve as substrate for the enzyme, with a cleavage site between two amino acids in the identification sequence in the peptide.

The peptide contains at least one quencher and at least one fluorophore. "Quenching" means reduction of the emission of the fluorophore due to interaction with the aforesaid quencher. A fluorescent dye is used as the fluorophore. Quenching causes a decrease in fluorescence quantum yield. The words "extinction" and "extinguishing molecule" or "extinguisher" are also used as synonyms for "quenching" and "quencher".

The amino acid tryptophan is used as quencher. Other amino acids, such as tyrosine or histidine, also exhibit slight fluorescence extinction, but do not have the strong quenching action of tryptophan.

The fluorescent dye is selected on the basis that its fluorescence can be extinguished by tryptophan. Furthermore, it should be possible for the fluorescent dye to be coupled covalently to peptides or proteins. As a rule the fluorophore is coupled to an amino acid.

Attainment of high sensitivity of the test requires targeted selection of the peptide sequence: the quencher must be arranged on one side of the cleavage site, with the fluorophore on the other side of the cleavage site. The sequence must be selected so that the quencher and the fluorophore are sufficiently spatially close to one another, so long as the substrate has still not been cleaved by the enzyme at the cleavage site between quencher and fluorophore, to provide the possibility of at least partial extinction of the emission of the fluorophore. After cleavage of the substrate by the enzyme at the cleavage site between quencher and fluorophore, a definite increase in emission of the fluorophore must be possible.

Thus, the peptide or protein is not marked with the fluorescent dye on the tryptophan itself, but on another amino acid, which is separated from the tryptophan by the cleavage site. Furthermore, an amino acid other than tryptophan is chosen for coupling the fluorescent dye, e.g. lysine, arginine or cysteine. The fluorescent dye can also be coupled to one end of the peptide or protein.

The largest increase in fluorescence is obtained if the tryptophan and the dye-marked amino acid are located directly on either side of the cleavage site. For dye MR 121, for example, an increase in fluorescence by a factor of 10 can be observed after cleavage of the peptide by the enzyme.

Moreover, no tryptophan is to be arranged in adjacent positions on the same side of the cleavage site of the peptide sequence as the dye, and especially not in immediately adjacent positions, so that the dye is not quenched by this additional tryptophan.

Appropriate choice of substrate sequence makes it possible to mark the substrate with just one fluorescent dye, and not with at least two, as was necessary until now. This simplifies the synthesis of the substrate. In addition there is less disturbance of binding of the enzyme to the substrate by coupled dyes, resulting in greater specificity of binding between substrate and enzyme.

Finally, the peptide thus prepared and the enzyme to be detected are mixed in a solution. If binding occurs between peptide and peptidase, the peptide is cleaved at the cleavage site. As a result, the spatial distance between the fluorophore and the quencher becomes greater, and the emission of the fluorophore increases. This increase in emission is determined and serves for detecting those peptidases or proteases that bind to the identification sequence and can cleave the peptide there. Accordingly, the detection reaction is specific. It can be directed towards the detection of specific enzymes by varying the peptide sequence.

In particular, the test can detect enzymes specifically, even when other types of enzymes are also present in the solution. For example, the enzyme trypsin can be detected in a solution that also contains elastase and chymotrypsin.

If the temporal course of the increase in emission is traced, the concentration of the enzyme can be determined quantitatively. Using the test as claimed in the invention, it is even possible to detect proteases or peptidases at a concentration of $10^{\wedge}-15$ mol/l.

As dyes, consideration may be given to all fluorescent dyes that are measurably extinguished in their fluorescence by the amino acid tryptophan. Dyes in the classes of oxazine derivatives (e.g. MR 121, JA 242, JA 243) and rhodamines (e.g. JA 165, JA 167, JA 169), which absorb and emit in the red region of the spectrum of visible light [see, for example, Müller R., Zander C., Sauer M., Deimel M., Ko D. S., Siebert S., Arden-Jacob J., Deltau G., Marx N. J., Drexhage K. H., Wolfrum J. Chem. Phys. Let. 1996, 262, 716-722] are particularly suitable. These red dyes are extinguished by tryptophan by one to two orders of magnitude better than other dyes.

When red dyes are used there is a marked increase in sensitivity, because otherwise the autofluorescence of biologically relevant proteins, e.g. blood sera and ascites, which mostly occurs in the green region of the visible spectrum, makes sensitive detection more difficult. With the method as claimed in the invention, sensitive tests can also be carried out on these biologically relevant samples, even on undiluted blood sera.

The aim is also achieved by a second test for the detection of exopeptidases (enzyme).

Once again a peptide is prepared. This time the peptide contains at least one group that contains a quencher and a fluorophore on different amino acids. Once again the amino acid tryptophan is used as the quencher. A fluorescent dye is again used as the fluorophore. A fluorescent dye is chosen that can be coupled covalently to peptides or proteins. Furthermore, the fluorescence of the dye can be extinguished by tryptophan.

The sequence of the peptide must be selected in such a way that the quencher and the fluorophore are spatially sufficiently close together, so long as the amino acids carrying the quencher or the fluorescent dye have not yet been separated by the enzyme, to ensure the possibility of an at least partial extinction of the emission of the fluorophore. Moreover, after separation of the amino acids carrying the quencher or the fluorescent dye by the enzyme, a sufficient spatial distance must be provided between any other quencher and the fluorophore, to achieve an at least partial increase in emission of the fluorophore.

The peptide prepared in this way is mixed in a solution with the enzyme to be detected. The intensity of the emission of the fluorophore in the solution is determined.

In many aspects this test corresponds to that already described for detecting an endopeptidase. It is, however, easier to detect an exopeptidase.

The exopeptidase digests the protein or peptide from its end. It detaches one amino acid after another. A tryptophan is also detached, among others. The dye coupled to an amino acid in the vicinity is therefore no longer extinguished, and there is an increase in fluorescence. The same applies when the amino acid is detached first with the dye.

If the substrate contains a multiplicity of tryptophan-dye groups, an increase in fluorescence can be observed repeatedly. The effect is then a multiple increase in fluorescence.

Once again, the aforementioned red dyes can be used advantageously.

The aim is finally achieved by a third test for the detection of endopeptidases (enzyme). This test again has many similarities and some decisive differences.

First a peptide is prepared. A group that prevents an exopeptidase from digesting the peptide is arranged at one end of the peptide. The group at the end of the peptidase that prevents the digestion of the peptide by an exopeptidase is also called a stop group or stop molecule. This can be, for example, D-amino acids, DNA or PNA, which are not cleaved by the exopeptidase.

Another possibility for providing a stop group is for an amino acid or amino acid sequence that is not cleaved by the exopeptidase to be arranged at the end of the peptide, by an appropriate choice of peptide sequence. The carboxypeptidase A as exopeptidase, for example, does not cleave beyond the amino acid proline at the end of a peptide. The arrangement of an ordinary amino acid as stop group facilitates synthesis of the peptide.

The exopeptidase can thus be present in solution with the peptide or protein, without the latter being attacked.

In addition the peptide contains an identification sequence of the endopeptidase that is to be detected and can therefore serve as substrate for the enzyme, yielding a cleavage site between two amino acids in the identification sequence in the peptide.

Viewed from the stop group in the sequence of the peptide on the other side of the cleavage site, the peptide contains at least one group that contains a quencher and a fluorophore on different amino acids.

The peptide sequence is chosen such that spatially the quencher and fluorophore are sufficiently close together, so long as the amino acids carrying the quencher and the fluorescent dye have not yet been separated by an exopeptidase, to ensure the possibility of an at least partial extinction of the emission of the fluorophore.

Moreover, it is necessary to ensure that after separation of the amino acids carrying the quencher and the fluorescent dye by an exopeptidase, a sufficient spatial distance is provided between any other quencher and the fluorophore, to achieve an at least partial increase in emission of the fluorophore.

Finally, the peptide thus prepared, the at least one exopeptidase and the endopeptidase that is to be detected are mixed in a solution. This results in binding between peptide as substrate and endopeptidase as enzyme. The peptide is cleaved at the cleavage site within the molecule. As a result the protective stop group at the end of the substrate is separated from the rest of the substrate. The residue that remains then no longer has a protective stop group, and an exopeptidase can digest the rest of the substrate.

Such an exopeptidase can be added to the solution in sufficient quantity, together with the substrate. It can thus be used as a kit together with the substrate.

By digestion by means of the exopeptidase, the quencher and fluorophore are separated. There is again an increase in fluorescence.

Amino acid sequences of any length can be present between the stop group and the region of the peptide or protein carrying the quencher-and-fluorophore groups, without impairing the sensitivity of detection. It is thus also possible to detect enzymes that possess a long identification sequence, such as HIV protease.

If a carboxypeptidase is used as exopeptidase, the stop group is placed at the C-terminal end of the peptide, so that subsequent digestion by the carboxypeptidase can take place. If, however, an aminopeptidase is used as exopeptidase, the stop group is placed at the N-terminal end of the peptide.

If the substrate contains a multiplicity of quencher-and-fluorophore groups, a multiple increase in fluorescence can again be observed. The measurement time can be shortened considerably as a result. There is at the same time a marked increase in the signal. The great advantage of multiple marking is that with a single cleavage and thus with a single endopeptidase to be detected, not only one, but many fluorophores are activated. As a result we obtain a more definite increase in signal in a much shorter time. This means that the increase in signal can even be measured with less sensitive instruments. There is also a shift of the limit of detection to lower values.

This test also detects endopeptidases specifically, with the other advantages that have already been mentioned.

Various dyes that are bound covalently to an amino acid can be selected as the fluorophore. A quencher can also be bound covalently to an amino acid. A suitable combination is for example the quencher DABCYL or guanosine and as fluorophore, for example, the dyes fluorescein, coumarin or eosins.

For this third test, once again the amino acid tryptophan can be used as quencher, together with a fluorescent dye as fluorophore. It must be possible for the fluorescent dye to couple covalently to peptides or proteins, and for its fluorescence to be extinguished by tryptophan. The advantages of this choice have already been explained. Once again it is possible to use red dyes.

Among other things, for this third test there are yet other possibilities for producing the quencher/fluorophore pair. The quencher can be at least one first fluorescent dye and the fluorophore at least one second fluorescent dye, provided they can both be coupled covalently to peptides or proteins. What is important is that the two dyes can extinguish one another when they are spatially close together. This can result from dimer formation or other mechanisms, such as energy transfer. After removal of the stop group by the endopeptidase that is to be detected, the exopeptidase digests the rest of the peptide chain, so that the dyes become farther apart and quenching is thus no longer possible. The resulting increase in intensity of fluorescence is measured.

Preferably all the aforementioned rhodamines and oxazines are suitable as dyes for this, and in addition cyanine derivatives (e.g. Cy 3, Cy 5, Cy 7, obtainable from Amersham Biosciences), all BODIPY dyes, all coumarins, fluorescein and Texas Red.

BRIEF DESCRIPTION OF THE DRAWING

The invention is explained in more detail below on the basis of examples of application, shown schematically in the diagrams. Reference numbers in the individual diagrams denote the same items.

FIG. 4A-C is a schematic representation of the detection reaction as claimed in FIG. 3 with multiple marking; and FIG. 5 shows the structural formulae of the dyes mentioned.

DETAILED DESCRIPTION OF PREFERRED EMBODIMENTS

First Test

Detection of an Endopeptidase

Figure 1:
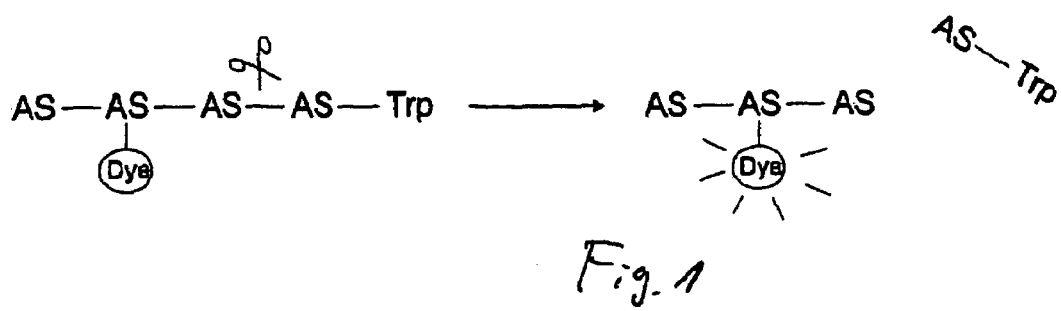
FIG. 1 is a schematic representation of the basic principle of the detection reaction.

FIG. 1 is a schematic representation of the principle of detection of an endopeptidase, which is represented in FIG. 1 by the scissors symbol. The peptide, consisting of four amino acids (AS) and tryptophan (Trp), serves as substrate.

A dye molecule (Dye), preferably MR 121, is coupled to the second amino acid from the left. Possibilities for coupling are described in [Bodanszky M.: "Peptide Chemistry: A Practical Textbook", Springer Verlag 1986] [Anderson G. W., Zimmerman J. E., Callahlan F. M.: "The use of esters of N-Hydroxysuccinimide in Peptide Synthesis", J. Am. Chem. Soc. 1964, 86, 1839-1842].

If, for example, we would like to detect the endopeptidase trypsin, which hydrolyzes the peptide bond between two arginines, the following peptide can be synthesized as substrate: Gln-Lys(MR 121)-Arg-Arg-Trp SEQ ID NO: 4, as shown schematically in FIG. 1.

Tryptophan acts as quencher on the dye. The mechanism of quenching is static quenching, in contrast to a dynamic impact quenching. The dye forms a complex with tryptophan, called a ground-state complex, which hardly fluoresces. In this ground-state complex there is electron transfer from tryptophan to the excited dye molecule.

Electron transfer will be explained briefly in the following, referring to FIG. 2. This depicts fluorescence quenching of the excited dye molecule F* by a tryptophan residue W. The black circles represent electrons. The HOMO (highest occupied molecular orbital) and the LUMO (lowest unoccupied molecular orbital) are shown in each case. The HOMO is the energetically highest molecular orbital occupied in the electronic ground state. The LUMO is the energetically lowest molecular orbital, unoccupied in the electronic ground state; it is as a rule the molecular orbital that is occupied in the first excited state.

Basically there are two possibilities for fluorescence quenching by photo-induced electron transfer. In the case shown on the left in FIG. 2, the tryptophan residue W acts as an electron donor (Donor). Following excitation of the fluorophore F*, an electron is transferred from the doubly occupied HOMO of the tryptophan residue W to the now singly occupied HOMO of the fluorophore F* (path 1). There is reduction of the excited fluorophore F* by the tryptophan residue W. The electron in the LUMO of fluorophore F* can then be transferred to the now singly occupied HOMO of tryptophan residue W (path 2). This case occurs between red dyes like MR 121 and tryptophan.

Figure 2:
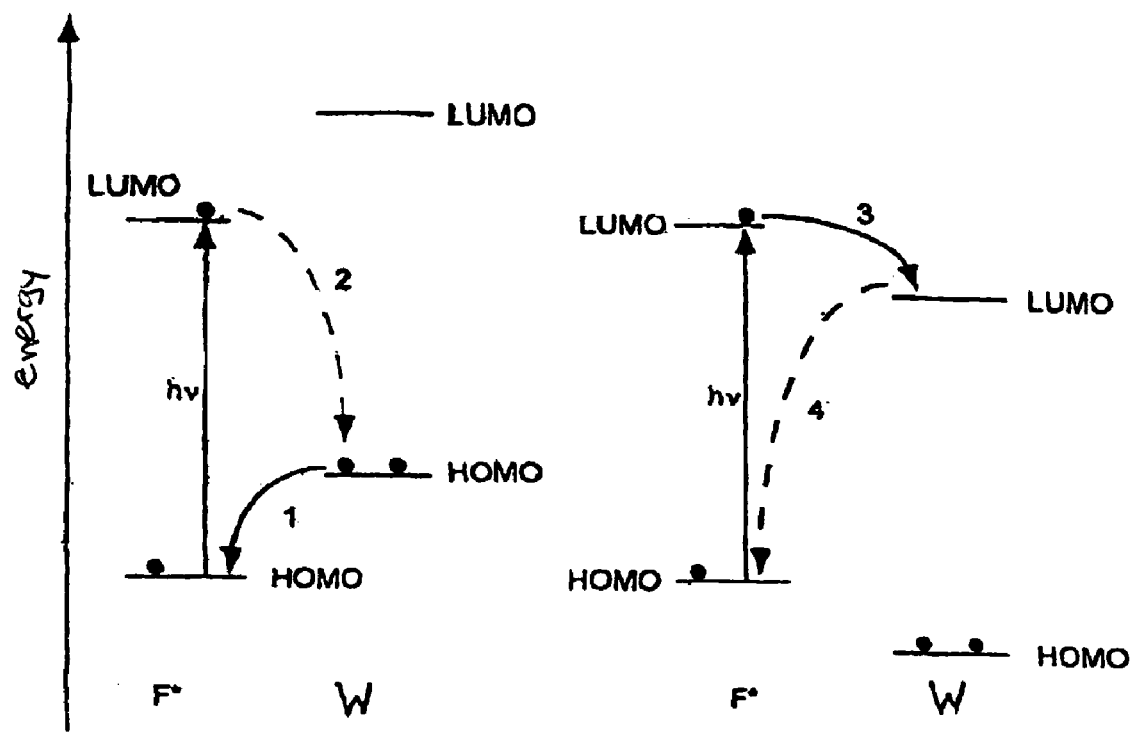
FIG. 2 is a schematic representation of the processes in photo-induced electron transfer.

In the case shown on the right in FIG. 2, the tryptophan residue W acts as an electron acceptor (Acceptor). The electron migrates from the singly occupied LUMO of the excited fluorophore F* to the unoccupied LUMO of tryptophan residue W (path 3). There is oxidation of the excited fluorophore F* by the tryptophan residue W. The electron in the LUMO of the tryptophan residue W can then return to the HOMO of the fluorophore (path 4).

In both cases, after electron transfer the electron can no longer return to the HOMO from the LUMO of the excited fluorophore F* by emitting a photon. The first excited state has been deactivated without radiation. The fluorescence is quenched.

With the red dyes under examination, tryptophan always acts as an electron donor. This knowledge makes it possible, for example, to choose suitable dyes on the basis of their electrochemically determined potentials.

The fluorescence signals are preferably detected in solution in a cuvette in conventional fluorescence spectrometers. This is generally called "homogeneous assay". More sensitive measurements can be carried out using confocal spectroscopy.

Instead of the fluorescence intensity, it is also possible to use the fluorescence lifetime for detection. The fluorescence lifetime is shorter in the quenched state than in the free, unquenched state.

Another possibility for detecting a quenched or unquenched state is measurement of changes in polarization. The polarization properties of emissions, e.g. fluorescence signals, can vary between a quenched and an unquenched state.

In the second and third test it is also possible to use FRET systems, i.e. pairs of dyes that extinguish each other by energy transfer. These often show different wavelengths in the quenched and unquenched state, which can be used for detection.

As excitation light sources it is preferable to use diode lasers, otherwise any other lasers or lamps with suitable wavelength. It is preferable to use pulsed diode lasers for determining the extinction time of the fluorophores.

As well as the so-called homogeneous assay, there is also a so-called heterogeneous assay. This generally denotes detection on a surface. The dye-marked peptides or proteins can be bound covalently to a surface at a C-end, an N-end or via amino acid residues (e.g. cysteine or lysine). Possible surfaces are for example modified glass surfaces (accordingly chips or biochips) or (possibly magnetic) beats. For this purpose the surfaces can be coated e.g. with linear and/or crosslinked polyethyleneglycols or hyaluronic acid, to prevent adsorption of the molecules.

If an amino acid, by which the peptide is bound to the surface, is located on the same side of the cleavage site as the dye, cleavage through the enzyme that is to be detected has the effect that the dye bound covalently to the surface stays back and its fluorescence can no longer be extinguished there. The fluorescence can then be detected evanescently or by means of surface screenings.

It is also possible to immobilize the peptide on the surface in such a way that the enzyme actually disrupts the bond between dye and surface as a result of the cleavage. The fluorescence of the unquenched dye can then be detected in the solution.

Second Test

Detection of an Exopeptidase

The second test described at the beginning for detecting an exopeptidase is carried out entirely similarly to the first test. The differences were described at the beginning.

Third Test

Detection of an Endopeptidase

Figure 3:
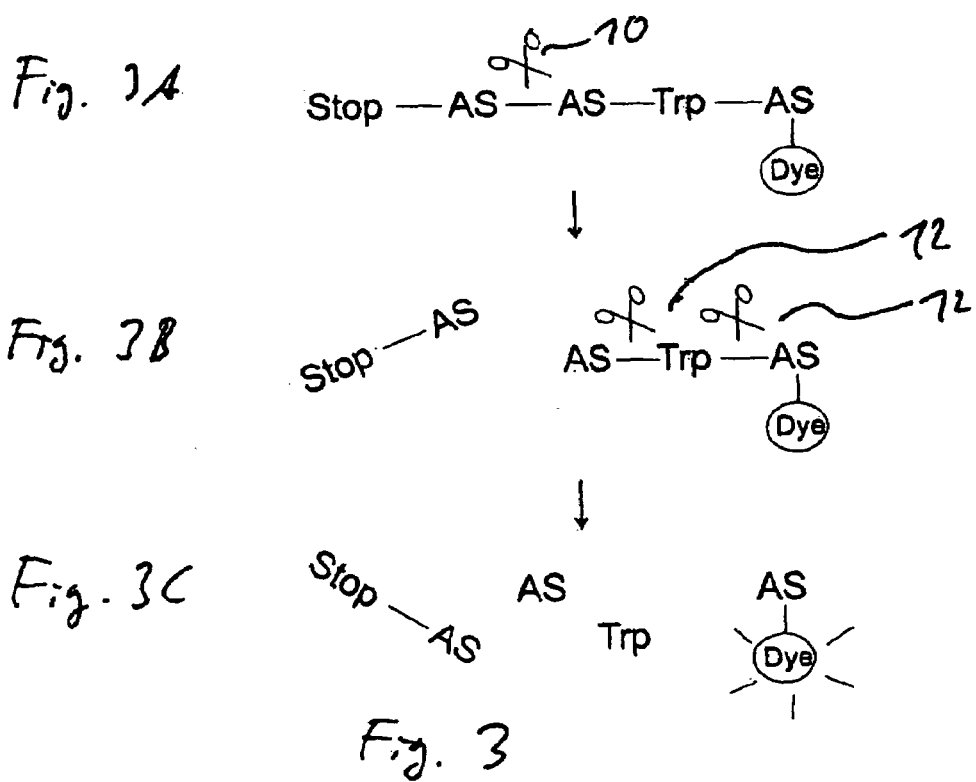
FIG. 3A-C is a schematic representation of the basic principle of a variant of the detection reaction.

FIG. 3 is a schematic representation of the principle of detection of an endopeptidase as claimed in the third test. The endopeptidase to be detected is represented in FIG. 3A by the scissors symbol 10. The peptide, consisting of a stop group (Stop), two amino acids (AS), tryptophan (Trp) and another amino acid (AS), to which a dye molecule (Dye) is coupled, preferably MR 121, serves as substrate.

The endopeptidase to be detected 10 cleaves the peptide between the two adjacent amino acids AS. This splits off the first stop group (Stop) together with an amino acid AS (see FIG. 3B). This makes it possible for the exopeptidase 12, which is also present in the solution and has up till now been prevented from digestion by the stop group (Stop), to digest the residual peptide.

The exopeptidase 12 successively splits off first an amino acid AS and then tryptophan (Trp). As a result of this, the dye (Dye) on the amino acid that remains (AS) is no longer located spatially close to the tryptophan, because the tryptophan diffuses away in the solution. Therefore the dye is no longer extinguished by tryptophan. Its fluorescence can be detected as a signal increase in the spectrometer.

For detecting HIV protease, the following peptide can be used: (N terminus) Lys(MR 121)-Trp-Ser-Gln-Asn-Tyr-Pro-Ile-Val-Gln-Pro-Pro (C terminus) SEQ ID NO: 5. This peptide contains the identification sequence for cleavage by HIV protease. This peptide can be used in combination with carboxypeptidase A, which does not cleave beyond proline. Therefore the two proline residues at the C terminus of the above peptide serve as a stop group. HIV protease cleaves between tyrosine and proline. Two fragments are produced: Lys(MR 121)-Trp-Ser-Gln-Asn-Tyr-OH SEQ ID NO: 6 and Pro-Ile-Val-Gln-Pro-Pro SEQ ID NO: 7. The stop group is removed thereby and carboxypeptidase A can digest the first fragment counting from the C terminus. This also separates the dye-marked lysine and tryptophan. An increase in fluorescence can be detected.

FIG. 4 shows the third test with signal intensification by multiple marking.

FIG. 4A shows the peptide, as in FIG. 3A, but with an alternating succession of tryptophan (Trp) and a dye-marked amino acid (AS+Dye). If the endopeptidase to be detected 10 splits off the stop group (Stop) (see FIG. 4B), the exopeptidase 12 can digest the peptide successively. In the process, tryptophan and free amino acid with the bound dye (AS+Dye) are released successively (see FIG. 4C). Thus, with one cleavage of the endopeptidase, a large number of dyes is released, whose emission is no longer extinguished. There is accordingly a rapid and strong signal increase. This shortens the measurement time, even for highly sensitive measurements, to minutes or seconds.

Finally, FIG. 5 shows the structure of the preferred dyes used, as mentioned at the beginning.

---

What is claimed is:

1. A peptide comprising:
an amino acid sequence comprising at least
a fluorophore and tryptophan for quenching fluorescence emitted from
the fluorophore, the fluorophore is not located on said tryptophan;
wherein the fluorophore is a fluorescent dye, which when covalently coupled to the peptide emits fluorescence that is quenched by said tryptophan;
wherein the fluorescent dye is an oxazine derivative or a rhodamine derivative, which absorbs and emits in a red region of visible light;
wherein the fluorophore and said tryptophan are in such spatial proximity
that as long as the tryptophan and the amino acid carrying the fluorescent dye have not been separated by an exopeptidase, quenching of the fluorescence of the fluorophore is realized; and
wherein after the tryptophan and the amino acid carrying the fluorescent dye are separated by the exopeptidase, an increase in fluorescent emission of the fluorophore is realized.

2. A method for the detection of an exopeptidase comprising the following steps:

mixing a peptide as claimed in claim 1 and the enzyme to be detected in a solution; and determining the intensity of emission of the fluorophore in the solution.

3. A device on which a peptide as claimed in claim 1 is immobilized.

4. A device having a surface on which a peptide is immobilized, said peptide comprising:

an amino acid sequence comprising at least a fluorophore and tryptophan for quenching fluorescence emitted from the fluorophore, the fluorophore is not located on said tryptophan; wherein the fluorophore is a fluorescent dye, which when covalently coupled to the peptide emits fluorescence that is quenched by said tryptophan;

wherein the fluorescent dye is an oxazine derivative or a rhodamine derivative, which absorbs and emits in a red region of visible light;

wherein the fluorophore and said tryptophan are in such spatial proximity that as long as the tryptophan and the amino acid carrying the fluorescent dye have not been separated by an exopeptidase, quenching of the emitted fluorescence of the fluorophore is realized; and wherein after the tryptophan and the amino acid carrying the fluorescent dye are separated by the exopeptidase, an increase in fluorescent emission of the fluorophore is realized; and wherein after cleavage by the exopeptidase to be detected, the fluorophore remains immobilized on the surface, whereas the quencher is no longer immobilized on the surface.

5. The device of claim 4, wherein the device is selected from the group consisting of glass beads, chips, biochips and magnetic beads; and wherein the surface the device is modified by layers of linear or networked polyethylene glycol or hyaluronic acid.

* * * * *